US006395513B1

(12) United States Patent
Foster et al.

(10) Patent No.: US 6,395,513 B1
(45) Date of Patent: *May 28, 2002

(54) CLOSTRIDIAL TOXIN DERIVATIVES ABLE TO MODIFY PERIPHERAL SENSORY AFFERENT FUNCTIONS

(75) Inventors: Keith Alan Foster, Wiltshire; Michael John Duggan, London; Clifford Charles Shone, Wiltshire, all of (GB)

(73) Assignees: The Speywood Laboratory, Ltd., London; Microbiological Research Authority, Wiltshire, both of (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/447,356

(22) Filed: Nov. 22, 1999

Related U.S. Application Data

(63) Continuation-in-part of application No. 08/945,037, filed as application No. PCT/GB96/00916 on Apr. 16, 1996, now Pat. No. 5,989,545.

(30) Foreign Application Priority Data

Apr. 21, 1995 (GB) .............................................. 9508204

(51) Int. Cl.[7] ........................ C12N 15/62; C12N 15/09; C12P 21/00; C07K 19/00
(52) U.S. Cl. .................... 435/69.3; 435/69.1; 435/69.7; 530/350
(58) Field of Search .............................. 435/69.1, 69.3, 435/69.7; 530/350

(56) References Cited

U.S. PATENT DOCUMENTS 5,989,545 A * 11/1999 Foster et al. ............. 424/183.1

FOREIGN PATENT DOCUMENTS

WO   93/04191   3/1993

OTHER PUBLICATIONS

Kim et al., Ribonuclease S–peptide as a carrier in fusion proteins, Protein Science 2(3), (1993), 348–356.
Rock et al., Overexpression and structure–function analysis of a bioengineered IL–2/IL–6 chimeric lymphokine, Protein Engineering vol. 5, (6):583–91.
O'Hare et al., Cytotoxicity of a recombinant ricin–A–chain fusion protein containing proteolytically–cleavable spacer sequence, FEBS Lett Oct. 29;273(1–2):200–4.
Lorberboum–Galaski et al., Cytotoxic activity of an interleukin 2–Pseudomonas exotoxin chimeric protein produced in *Escherichia coli*, Proc. Natl. Acad. Sci USA 85(6):1922–6.
John R. Murphy, Diphtheria–related peptide hormone gene fusions: A molecular genetic approach to chimeric toxin development, Cancer Treatment Res; 37:123–40.
Williams et al., Diphtheria toxin receptor binding domain substitution with interleukin–2: genetic construction and properties of a diptheria toxin–related interleukin–2 fusion protein, Protein Eng. 1(6):(1987):493–8.
Arora et al., Cytotoxic Effects of a Chimeric Protein Consisting of Tetanus Toxin Light Chain and Anthrax Lethal Factor in Non–neuronal Cells, Journal of Biol Chem:(1994):269(42):26265–71.
Brinkmann et al., A recombinant immunotoxin containing a disulfide–stabilized Fv fragment, Proc Natl Acad Sci USA, (1993); 90(1):7538–42.
Ulrich et al., "Human beta–nerve growth factor gene sequence highly homologous to that of mouse." Nature (1983), 303:821–825.
Borsani et al., cDNA sequence of human B–NGF, Nucleuic Acids Res. (1990), 18:4020.
Noda et al., "Isolation and structural organisation of the human preproenkephalin gene", Nature (1982) 297:431–434.
Comb et al., Primary structure of the human Met–and Leu–enkephalin precursor and its mRNA, Nature (1985), 295–663–666.
Takagaki et al., "Cloning and sequence analysis of cDNAs for human high molecular weight and low molecular weight prekininogens, Primary structures of two human prekininogens", J. Biol. Chem. (1985) 260:8601–8609.
Dicou et al., Expression of recombinant human nerve growth factor in *Escherichia coli*, Neurochem Int. 20, pp. 129–134.
Fujimori et al., Overproduction of biologically–active human nerve growth factor in *Escherichia coli*, Biosci–Biotechnol–Biochem, 56, (1992), 1985–1990.

* cited by examiner

*Primary Examiner*—Mary E. Mosher
(74) *Attorney, Agent, or Firm*—Foley & Lardner

(57) ABSTRACT

The invention relates to an agent specific for peripheral sensory afferents. The agent may inhibit the transmission of signals between a primary sensory afferent and a projection neuron by controlling the release of at least one neurotransmitter or neuromodulator from the primary sensory afferent. The agent may be used in or as a pharmaceutical for the treatment of pain, particularly chronic pain.

7 Claims, 4 Drawing Sheets

SEQUENCE LISTING

```
<160> NUMBER OF SEQ ID NOS:  11

<210> SEQ ID NO 1
<211> LENGTH: 120
<212> TYPE: PRT
<213> ORGANISM: Murine sp.

<400> SEQUENCE: 1
```

```
Ser Ser Ser His Pro Ile Phe His Arg Gly Glu Phe Ser Val Cys Asp
 1               5                  10                  15

Ser Val Ser Val Trp Val Gly Asp Lys Thr Thr Ala Thr Asp Ile Lys
            20                  25                  30

Gly Lys Glu Val Met Val Leu Gly Glu Val Asn Ile Asn Asn Ser Val
        35                  40                  45

Phe Lys Gln Tyr Phe Glu Thr Lys Cys Arg Asp Pro Asn Pro Val
    50                  55                  60

Asp Ser Gly Cys Arg Gly Ile Asp Ser Lys His Trp Asn Ser Tyr Cys
65                  70                  75                  80

Thr Thr Thr His Thr Phe Val Lys Ala Leu Thr Met Asp Gly Lys Gln
                85                  90                  95

Ala Ala Trp Arg Phe Ile Arg Ile Asp Thr Ala Cys Val Cys Val Leu
            100                 105                 110

Ser Arg Lys Ala Val Arg Arg Ala
        115                 120
```

<210> SEQ ID NO 2
<211> LENGTH: 360
<212> TYPE: RNA
<213> ORGANISM: Artificial Organism
<220> FEATURE:
<223> OTHER INFORMATION: Description of Artificial Organism:
      Back-translated bacterial codon usage sequence for NGF

<400> SEQUENCE: 2

```
uccuccuccc acccgaucuu ccaccguggu gaauucuccg uuugcgacuc cguuuccguu      60
uggguuggug acaaaaccac cgcuaccgac aucaaaggua agaaguuau g guucgggu     120
gaaguuaaca ucaacaacuc cguuuucaaa caguacuucu ucgaaaccaa a ugccgugac   180
ccgaacccgg uugacuccgg uugccguggu aucgacucca acacuggaa c uccuacugc   240
accaccaccc acaccuucgu uaaagcucug accauggacg guaaacaggc u gcuggcgu   300
uucauccgua ucgacaccgc uugcguuugc guucuguccc guaaagcugc u cgucgugcu  360
```

<210> SEQ ID NO 3
<211> LENGTH: 241
<212> TYPE: PRT
<213> ORGANISM: Murine sp.

<400> SEQUENCE: 3

```
Met Ser Met Leu Phe Tyr Thr Leu Ile Thr Ala Phe Leu Ile Gly Ile
 1               5                  10                  15

Gln Ala Glu Pro His Ser Glu Ser Asn Val Pro Ala Gly His Thr Ile
            20                  25                  30

Pro Gln Val His Trp Thr Lys Leu Gln His Ser Leu Asp Thr Ala Leu
        35                  40                  45

Arg Arg Ala Arg Ser Ala Pro Ala Ala Ile Ala Ala Arg Val Ala
50                  55                  60

Gly Gln Thr Arg Asn Ile Thr Val Asp Pro Arg Leu Phe Lys Lys Arg
65                  70                  75                  80

Arg Leu Arg Ser Pro Arg Val Leu Phe Ser Thr Gln Pro Pro Arg Glu
            85                  90                  95

Ala Ala Asp Thr Gln Asp Leu Asp Phe Glu Val Gly Gly Ala Ala Pro
            100                 105                 110

Phe Asn Arg Thr His Arg Ser Lys Arg Ser Ser Ser His Pro Ile Phe
        115                 120                 125
```

His Arg Gly Glu Phe Ser Val Cys Asp Ser V al Ser Val Trp Val Gly
    130                 135                 140

Asp Lys Thr Thr Ala Thr Asp Ile Lys Gly L ys Glu Val Met Val Leu
145                 150                 155                 160

Gly Glu Val Asn Ile Asn Asn Ser Val Phe L ys Gln Tyr Phe Phe Glu
                165                 170                 175

Thr Lys Cys Arg Asp Pro Asn Pro Val Asp S er Gly Cys Arg Gly Ile
            180                 185                 190

Asp Ser Lys His Trp Asn Ser Tyr Cys Thr T hr Thr His Thr Phe Val
        195                 200                 205

Lys Ala Leu Thr Met Asp Gly Lys Gln Ala A la Trp Arg Phe Ile Arg
    210                 215                 220

Ile Asp Thr Ala Cys Val Cys Val Leu Ser A rg Lys Ala Val Arg Arg
225                 230                 235                 240

Ala

<210> SEQ ID NO 4
<211> LENGTH: 723
<212> TYPE: RNA
<213> ORGANISM: Artificial Organism
<220> FEATURE:
<223> OTHER INFORMATION: Description of Artificial  Organism:
      Back-translated bacterial codon usage sequence for pro-NGF

<400> SEQUENCE: 4
auguccaugc uguucuacac ccugaucacc gcuuccuga ucgguaucca g gcugaaccg      60 cacuccgaau ccaacguucc ggcuggucac accaucccgc agguucacug g accaaacug    120 cagcacuccg uggacaccgc ucugcgucgu gcucguuccg cuccggcugc u gcuaucgcu   180 gcucguguug cuggucagac ccguaacauc accguugacc gcgucuguu c aaaaaacgu    240 cgucugcguu ccccgcgugu ucuguucucc acccagccgc cgcugaagc u gcugacacc    300 caggaccugg acuucgaagu ggugguguu cuccguuca accguaccca c cguuccaaa    360 cguuccuccu cccacccgau cuuccaccgu ggugaauuca ccguuugcga c uccguuucc   420 guuuggguug ugacaaaac caccgcuacc gacaucaaag guaagaaguu a ugguucug    480 ggugaaguua acaucaacaa cuccguuuuc aaacaguacu ucuucgaaac c aaaugccgu    540 gacccgaacc cgguugacuc cgguugccgu gguaucgacu ccaaacacug g aacuccuac    600 ugcaccacca cccacaccuu cguuaaagcu cugaccaugg acgguaaaca g gcugcuugg    660 cguuucaucc guaucgacac cgcuugcguu ugcguucugu cccguaaagc u guucgucgu   720 gcu                                                                    723

<210> SEQ ID NO 5
<211> LENGTH: 5
<212> TYPE: PRT
<213> ORGANISM: Homo sapiens

<400> SEQUENCE: 5

Tyr Gly Gly Phe Leu
  1               5

<210> SEQ ID NO 6
<211> LENGTH: 15
<212> TYPE: RNA
<213> ORGANISM: Artificial Organism
<220> FEATURE:
<223> OTHER INFORMATION: Description of Artificial  Organism: Bacterial
      coding sequence -continued

```
<400> SEQUENCE: 6
uacggugguu uccug                                                      15

<210> SEQ ID NO 7
<211> LENGTH: 5
<212> TYPE: PRT
<213> ORGANISM: Homo sapiens

<400> SEQUENCE: 7

Tyr Gly Gly Phe Met
 1               5

<210> SEQ ID NO 8
<211> LENGTH: 15
<212> TYPE: RNA
<213> ORGANISM: Artificial Organism
<220> FEATURE:
<223> OTHER INFORMATION: Description of Artificial  Organism: Bacterial
      coding sequence

<400> SEQUENCE: 8
uacggugguu ucaug                                                      15

<210> SEQ ID NO 9
<211> LENGTH: 9
<212> TYPE: PRT
<213> ORGANISM: Homo sapiens

<400> SEQUENCE: 9

Arg Pro Pro Gly Phe Ser Pro Phe Arg
 1               5

<210> SEQ ID NO 10
<211> LENGTH: 27
<212> TYPE: RNA
<213> ORGANISM: Artificial Organism
<220> FEATURE:
<223> OTHER INFORMATION: Description of Artificial  Organism: Bacterial
      coding sequence

<400> SEQUENCE: 10
cguccgccgg guuucucccc guuccgu                                         27

<210> SEQ ID NO 11
<211> LENGTH: 7
<212> TYPE: PRT
<213> ORGANISM: Artificial Organism
<220> FEATURE:
<223> OTHER INFORMATION: Description of Artificial  Organism: Spacer
      molecule

<400> SEQUENCE: 11

Pro Pro Pro Ile Glu Gly Arg
 1               5
```

CLOSTRIDIAL TOXIN DERIVATIVES ABLE TO MODIFY PERIPHERAL SENSORY AFFERENT FUNCTIONS

This application is a continuation-in-part of application Ser. No. 08/945,037, filed Jan. 12, 1998, now U.S. Pat. No. 5,989,545, which is a National Stage filing of PCT/GB96/00916, which has an international filing date of Apr. 16, 1996. PCT/GB96/00916 is based on UK application 9508204.6, which was filed Apr. 21, 1995.

TECHNICAL FIELD

This invention relates to a novel agent that is able to modify peripheral afferent function. The agent may inhibit neurotransmitter release from discrete populations of neurons, and thereby reduce, or preferably prevent, the transmission of afferent pain signals from peripheral to central pain fibres. The agent may be used in or as a pharmaceutical for the treatment of pain, particularly chronic pain.

BACKGROUND

The sense of touch has traditionally been regarded as one of the five classical senses, but in reality it is highly complex, transducing a number of different sensations. These sensations are detected in the periphery by a variety of specialised nerve endings and associated structures. Some of these are specific for mechanical stimuli of various sorts such as touch, pressure, vibration, and the deformation of hairs or whiskers. Another class of nerves is able to detect temperatures, with different fibres being activated by heat and cold. A further population of nerve endings is not normally excited by mild stimuli, but by strong stimuli only. Sensory nerves of this category often respond to more than one stimulus, and are known as high-threshold polymodal fibres. They may be used to sense potentially damaging situations or objects. The polymodal fibres also transduce chemical signals such as the "burning" sensation evoked by acid. Thus, the sense of touch can transmit a very detailed description of objects and serve to both inform and warn of events.

The transduction of sensory signals from the periphery to sensation itself is achieved by a multi-neuronal pathway and the information processing centres of the brain. The first nerve cells of the pathway involved in the transmission of sensory stimuli are called primary sensory afferents. The cell bodies for the primary sensory afferents from the head and some of the internal organs reside in various of the ganglia associated with the cranial nerves, particularly the trigeminal nuclei and the nucleus of the solitary tract. The cell bodies for the primary sensory afferents for the remainder of the body lie in the dorsal root ganglia of the spinal column. The primary sensory afferents and their processes have been classified histologically; the cell bodies fall into two classes: A-type are large (60–120 $\mu$m in diameter) while B-type are smaller (14–30 $\mu$m) and more numerous. Similarly the processes fall into two categories: C-fibres lack the myelin sheath that A-fibres possess. A-fibres can be further subdivided into A$\beta$-fibres, that are large diameter with well developed myelin, and A$\delta$-fibres, that are thinner with less well developed myelin. It is generally believed that A$\beta$-fibres arise from A-type cell bodies and that A$\delta$- and C-fibres arise from B-type cell bodies. These classifications can be further extended and subdivided by studying the selective expression of a range of molecular markers.

Functional analyses indicate that under normal circumstances A$\beta$-fibres transmit the senses of touch and moderate temperature discrimination, whereas the C-fibres are mainly equivalent to the polymodal high-threshold fibres mentioned above. The role of A$\delta$-fibres is less clear as they seem to have a variety of responsive modes, with both high and low thresholds.

After the activation of the primary sensory afferents the next step in the transduction of sensory signals is the activation of the projection neurons, which carry the signal to higher parts of the central nervous system such as the thalamic nuclei. The cell bodies of these neurons (other than those related to the cranial nerves) are located in the dorsal horn of the spinal cord. This is also where the synapses between the primary afferents and the projection neurons are located. The dorsal horn is organised into a series of laminae that are stacked, with lamina I being most dorsal followed by lamina II, etc. The different classes of primary afferents make synapses in different laminae. For cutaneous primary afferents, C-fibres make synapses in laminae I and II, A$\delta$-fibres in laminae I, II, and V, and A$\beta$-fibres in laminae III, IV, and V. Deeper laminae (V–VII, X) are thought to be involved in the sensory pathways arriving from deeper tissues such as muscles and the viscera.

The predominant neurotransmitter at the synapses between primary afferents and projection neurons is glutamate, although importantly the C-fibres contain several neuropeptides such as substance P and calcitonin-gene related peptide (CGRP). A-fibres may also express neuropeptides such as neuropeptide Y under some circumstances.

The efficiency of transmission of these synapses can be altered via descending pathways and by local interneurons in the spinal cord. These modulatory neurons release a number of mediators that are either inhibitory (e.g. opioid peptides, glycine) or excitatory (e.g. nitric oxide, cholecystokinin), to provide a mechanism for enhancing or reducing awareness of sensations.

A category of sensation that requires such physiological modulation is pain. Pain is a sensation that can warn of injury or illness, and as such is essential in everyday life. There are times, however, when there is a need to be able to ignore it, and physiologically this is a function of, for example, the opioid peptides. Unfortunately, despite these physiological mechanisms, pain can continue to be experienced during illnesses or after injuries long after its utility has passed. In these circumstances pain becomes a symptom of disease that would be better alleviated.

Clinically, pain can be divided into three categories: (1) Acute pain, usually arising from injury or surgery that is expected to disappear when that injury is healed. (2) Chronic pain arising from malignant disease; the majority of people with metastatic cancer have moderate to severe pain and this is resolved either by successful treatment of the disease or by the death of the patient. (3) Chronic pain not caused by malignant disease; this is a heterogeneous complaint, caused by a variety of illnesses, including arthritis and peripheral neuropathies, that are usually not life-threatening but which may last for decades with increasing levels of pain.

The physiology of pain that results from tissue damage is better understood than that which is caused by central nervous system defects. Under normal circumstances the sensations that lead to pain are first transduced by the A$\delta$- and C-fibres that carry high threshold signals. Thus the synapses in laminae I and II are involved in the transmission of the pain signals, using glutamate and the peptides released by C-fibres to produce activation of the appropriate projection neurons. There is, however, evidence that in some chronic pain states other A-fibres (including Aβ-fibres) can carry pain signals, and thus act as primary nociceptive afferents, for example in the hyperalgesia and allodynia associated with neuropathic pain. These changes have been associated with the expression of peptides such as neuropeptide Y in A fibres. During various chronic pain conditions the synapses of the various sensory afferents with projection neurons may be modified in several ways: there may be changes in morphology leading to an increase in the number of synapses, the levels and ratios of the different peptides may change, and the sensitivity of the projection neuron may change.

Given the enormity of the clinical problem presented by pain, considerable effort has been expended in finding methods for its alleviation. The most commonly used pharmaceuticals for the alleviation of pain fall into two categories: (1) Non-steroidal anti-inflammatory drugs (NSAIDs), including aspirin and ibuprofen; (2) Opioids, including morphine.

NSAIDs have their main analgesic action at the periphery by inhibiting the production of prostaglandins by damaged tissues. Prostaglandins have been shown to be peripheral mediators of pain and inflammation and a reduction in their concentration provides relief to patients. This is especially the case in mild arthritic disease, where inflammation is a major cause of pain. It has been suggested that prostaglandins are involved in the mediation of pain in the spinal cord and the brain; this may explain why NSAIDs have analgesic effects in some pain states that do not involve inflammation or peripheral tissue damage. As prostaglandins, however, are only one of several mediators of pain NSAIDs alone are only effective in reducing some types of mild pain to acceptable levels. They are regarded as having a ceiling of activity above which increasing doses do not give increasing pain relief. Furthermore they have side effects that limit their usefulness in chronic complaints. The use of NSAIDs is associated with irritation of the gastrointestinal tract and prolonged use may lead to the development of extensive ulceration of the gut. This is particularly true in elderly patients who form the largest cohort of patients with, for example, arthritis.

Opioids act at the level of the spinal cord to inhibit the efficiency of neurotransmission between the primary nociceptive fibres (principally C-fibres) and the projection neurons. They achieve this by causing a prolonged hyperpolarization of both elements of these synapses. The use of opioids is effective in alleviating most types of acute pain and chronic malignant pain. There are, however, a number of chronic malignant pain conditions which are partly or completely refractory to opioid analgesia, particularly those which involve nerve compression, e.g. by tumour formation. Unfortunately opioids also have unwanted systemic side-effects including: (1) depression of the respiratory system at the level of the respiratory centres in the brain stem; (2) the induction of constipation by a variety of effects on the smooth musculature of the gastro-intestinal tract; and (3) psychoactive effects including sedation and the induction of euphoria. These side effects occur at doses similar to those that produce analgesia and therefore limit the doses that can be given to patients.

Delivery of opioids at the spinal level can reduce the side-effect profile, but requires either frequently repeated spinal injections or fitting of a catheter, both of which carry increased risk to the patient. Fitting of a catheter requires that the patient is essentially confined to bed thus further restricting their quality of life.

The use of opioids for the treatment of some other types of chronic pain is generally ineffective or undesirable. Examples include the pain associated with rheumatoid arthritis and neuromas that develop after nerve injury. The undesirable nature of opioid treatment in these patients is related not only to side-effects already mentioned and the probable duration of the disease but also to the fourth major side-effect of the opioids: dependence. Opioids such as morphine and heroin are well-known drugs of abuse that lead to physical dependence, this last side-effect involves the development of tolerance: the dose of a drug required to produce the same analgesic effect increases with time. This may lead to a condition in which the doses required to alleviate the pain are life-threatening due to the first three side-effects.

Although NSAIDs and opioids have utility in the treatment of pain there is general agreement that they are often not appropriate for the adequate treatment of pain, particularly chronic and severe pains.

Other treatments are also used, particularly for the treatment of chronic severe pain including surgical lesions of the pain pathways at several levels from peripheral nerves through dorsal root section and cordotomy to pituitary destruction. These are, however, mostly severe operations that are all associated with significant risk to the patient.

It can be seen, therefore, that there remains a significant need for the development of new classes of pharmaceuticals for the treatment of pain of many types. The desired properties of such new therapies can be briefly expressed as follows: (1) the ability to provide significant relief of pain including severe pain; (2) the lack of systemic side effects that significantly impair the patient's quality of life; (3) long-lasting actions that do not require frequent injections or long-term catheterisation of patients; (4) provision of agents that do not lead to tolerance and associated dependence.

STATEMENT OF INVENTION

The present invention relates to an agent which can reduce and preferably prevent the transmission of pain signals from the periphery to the central nervous system, thereby alleviating the sensation of pain. Specifically, the invention can provide an agent which can reduce and preferably prevent the transmission of pain signals from nociceptive afferents to projection neurons. More specifically, the invention can provide an agent which can inhibit the exocytosis of at least one neurotransmitter or neuromodulator substance from at least one category of nociceptive afferents.

In a first aspect of the invention, there is provided an agent which can be administered systemically, and can specifically target defined populations of nociceptive afferents to inhibit the release of at least one neurotransmitter or neuromodulator from the synaptic terminals of nerves.

In a second aspect of the invention, there is provided an agent which can be locally administered at the periphery, and which is able to inhibit the release of at least one neurotransmitter or neuromodulator from the synaptic terminals of nociceptive afferents transmitting the pain signal from the periphery.

In a third aspect of the invention, an agent is provided which can be administered into the spinal cord, and which can inhibit the release of at least one neurotransmitter or neuromodulator from the synaptic terminals of nociceptive afferents terminating in that region of the spinal cord.

In a fourth aspect of the invention, there is provided an agent which can specifically target defined populations of afferent neurons, so that the effect of the agent is limited to that cell type.

In a fifth aspect of the invention, there is provided a method of treatment of pain which comprises administering an effective dose of the agent according to the invention.

In a sixth aspect of the invention, the agent can be expressed recombinantly as a fusion protein which includes the required components of the agent.

Definitions

Without wishing to be limited by the definitions set down, it is intended in this description that the following terms have the following meanings:

Light chain means the smaller of the two polypeptide chains which form clostridial neurotoxins; it has a molecular mass of approximately 50 kDa and is commonly referred to as L-chain or simply L.

Heavy chain means the larger of the two polypeptide chains which form clostridial neurotoxins; it has a molecular mass of approximately 100 kDa and is commonly referred to as H-chain or simply H.

$H_C$ fragment means a fragment derived from the H-chain of a clostridial neurotoxin approximately equivalent to the carboxy-terminal half of the H-chain, or the domain corresponding to that fragment in the intact H-chain. It contains the domain of the natural toxin involved in binding to motor neurons.

$H_N$ fragment means a fragment derived from the H-chain of a clostridial neurotoxin approximately equivalent to the amino-terminal half of the H-chain, or the domain corresponding to that fragment in the intact in the H-chain. It contains a domain involved in the translocation of the L-chain across endosomal membranes.

$LH_N$ means a fragment derived from a clostridial neurotoxin that contains the L-chain, or a functional fragment thereof coupled to the $H_N$ fragment. It is commonly derived from the intact neurotoxin by proteolysis.

Targeting Moiety (TM) means any chemical structure of an agent which functionally interacts with a binding site causing a physical association between the agent and the surface of a primary sensory afferent.

Binding site (BS) means a structure on the surface of a cell with which exogenous molecules are able to interact in such a way as to bring about a physical association with the cell.

Primary sensory afferent is a nerve cell that can carry sensory information from the periphery towards the central nervous system.

Primary nociceptive afferent is a nerve cell that can carry sensory information from the periphery towards the central nervous system, where that information can result in a sensation of pain.

DETAILED DESCRIPTION OF THE INVENTION

Figure 1:
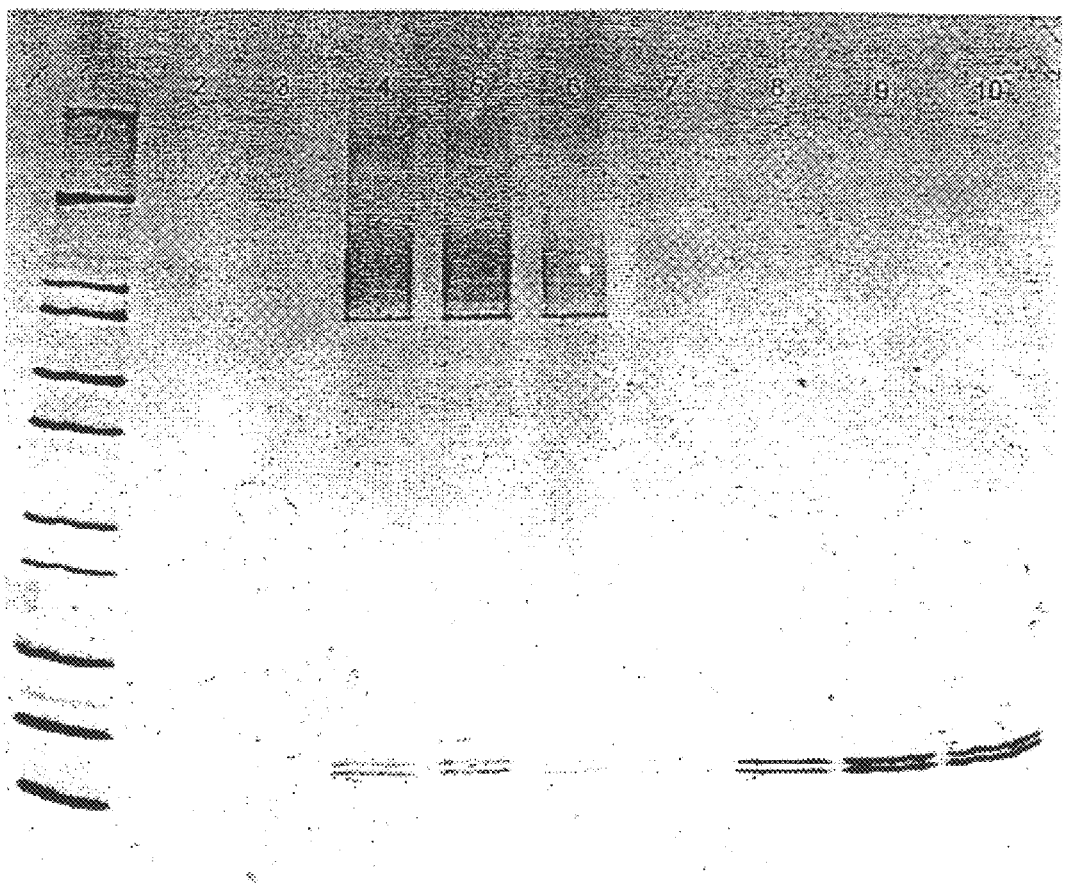
FIG. 1 shows a Coomassie stain of an SDS-PAGE analysis of the fractions from size-exclusion chromatography of the products of the coupling reaction between derivatized Nerve Growth Factor (NGF) and derivatized $LH_N$ from BoNT/A.

It can be seen that, an agent for reducing or preventing the transmission of pain signals from peripheral, nociceptive afferent neurons to projection neurons has many potential applications in the reduction of the sensation of pain, particularly of severe, chronic pain.

According to the invention, there is provided an agent which can inhibit the release of at least one neurotransmitter or neuromodulator or both from the synaptic terminals of nociceptive afferents.

The agent has a number of discrete functions:
1) It binds to a surface structure (the Binding Site [BS]) which is characteristic of, and has a degree of specificity for, nociceptive afferent neurons.
2) It enters the neuron. The entry of molecules into a cell can occur by a process of endocytosis. Only certain cell surface BSs undergo endocytosis, and preferably the BS to which the agent binds is one of these. In one aspect of this invention, the BS is present on the peripheral, sensory fibres of the nociceptive afferent neuron and, following internalization, undergoes retrograde transport to the cell body and central processes of the neuron, in such a manner that the agent is also delivered to these regions of the neuron. In another aspect of this invention, the BS to which the agent binds is present on the central processes or cell body of the nociceptive afferent neuron.
3) The agent enters the cytosol.
4) The agent modifies components of the exocytotic machinery present in the synaptic terminals of the central processes of those neurons, such that the release of at least one neurotransmitter or neuromodulator from the synaptic terminal is reduced or preferably prevented.

Surprisingly, an agent of the present invention can be produced by modifying a clostridial neurotoxin or fragment thereof.

The clostridial neurotoxins are proteins with molecular masses of the order of 150 kDa. They are produced by various species of the genus Clostridium, most importantly C. tetani and several strains of C. botulinum. There are at present eight different classes of the neurotoxins known: tetanus toxin, and botulinum neurotoxin in its serotypes A, B, C1, D, B, F and G, and they all share similar structures and modes of action. The clostridial neurotoxins are synthesized by the bacterium as a single polypeptide that is modified post-translationally to form two polypeptide chains joined together by a disulphide bond. The two chains are termed the heavy chain (H), which has a molecular mass of approximately 100 kDa, and the light chain (L), which has a molecular mass of approximately 50 kDa. The clostridial neurotoxins bind to an acceptor site on the cell membrane of the motor neuron at the neuromuscular junction and are internalised by an endocytotic mechanism. The internalised clostridial neurotoxins possess a highly specific zinc-dependent endopeptidase activity that hydrolyses a specific peptide bond in at least one of three proteins, synaptobrevin, syntaxin or SNAP-25, which are crucial components of the neurosecretory machinery, and this activity of the clostridial toxins results in a prolonged muscular paralysis. The zinc-dependent endopeptidase activity of clostridial neurotoxins is found to reside in the L-chain. The clostridial neurotoxins are highly selective for motorneurons due to the specific nature of the acceptor site on those neurons. The specific neuromuscular junction binding activity of clostridial neurotoxins is known to reside in the carboxy-terminal portion of the heavy chain component of the dichain neurotoxin molecule, a region known as $G_H$.

Surprisingly, by covalently linking a clostridial neurotoxin, or a hybrid of two clostridial neurotoxins, in which the $H_C$ region of the H-chain has been removed or modified, to a new molecule or moiety, the Targeting Moiety (TM, that binds to a BS on the surface of sensory neurons, a novel agent capable of inhibiting the release of at least one neurotransmitter or neuromodulator from nociceptive afferents is produced. A further surprising aspect of the present invention is that if the L-chain of a clostridial neurotoxin, or a fragment of the L-chain containing the endopeptidase activity, is covalently linked to a TM which can also effect internalisation of the L-chain, or fragment thereof, into the cytoplasm of a sensory neuron, this also produces a novel agent capable of inhibiting the release of at least one neurotransmitter or neuromodulator. The covalent linkages used to couple the component parts of the agent may include appropriate spacer regions.

The TM provides specificity for the BS on the nociceptive afferent neuron. The TM component of the agent can comprise one of many cell binding molecules, including, but not limited to, antibodies, monoclonal antibodies, antibody fragments (Fab, F(ab)'$_2$, Fv, ScFv, etc.), lectins and ligands to the receptors for hormones, cytokines, growth factors or neuropeptides. A list of possible TMs is given in Table 1, this list is illustrative and is not intended to be limiting to the scope of TMs which could fulfil the requirements of this invention. In one embodiment of the invention the TM binds to a BS which undergoes retrograde transport.

It is known in the art that the $H_C$ portion of the neurotoxin molecule can be removed from the other portion of the heavy chain, known as $H_N$, such that the $H_N$ fragment remains disulphide linked to the light chain (L-chain) of the neurotoxin molecule to provide a fragment known as $LH_N$. Thus, in one embodiment of the present invention the $LH_N$ fragment of a clostridial neurotoxin is covalently linked, using linkages which may include one or more spacer regions, to a TM.

In another embodiment of the invention, the $H_C$ domain of a clostridial neurotoxin is mutated or modified, e.g. by chemical modification, to reduce or preferably incapacitate its ability to bind the neurotoxin to receptors at the neuromuscular junction. This modified clostridial neurotoxin is then covalently linked, using linkages which may include one or more spacer regions, to a TM.

In another embodiment of the invention, the heavy chain of a clostridial neurotoxin, in which the $H_C$ domain is mutated or modified, e.g. by chemical modification, to reduce or preferably incapacitate its ability to bind the neurotoxin to receptors at the neuromuscular junction is combined with the L-chain of a different clostridial neurotoxin. The hybrid, modified clostridial neurotoxin is then covalently linked, using linkages which may include one or more spacer regions, to a TM.

In another embodiment of the invention, the $H_N$ portion of a clostridial neurotoxin is combined with the L-chain of a different clostridial neurotoxin. The hybrid $LH_N$ is then covalently linked, using linkages which may include one or more spacer regions, to a TM.

In another embodiment of the invention the light chain of a clostridial neurotoxin, or a fragment of the light chain containing the endopeptidase activity, is linked, using linkages which may include one or more spacer regions, to a TM which can also effect the internalization of the light chain, or fragment thereof containing endopeptidase activity, into the cytoplasm of the cell.

In another embodiment of the invention the agent is expressed recombinantly as a fusion protein which includes an appropriate fragment of a Targeting Moiety in addition to any desired spacer domains. The recombinantly expressed agent may be derived wholly from the gene encoding one serotype of neurotoxin or be a chimaera derived from the genes encoding two different serotypes.

In this embodiment, a genetic construct is employed which encodes the clostridial neurotoxin, or fragment thereof, and the TM. Reference to the clostridial neurotoxin Includes reference to a fragment thereof having the desired protease activity.

The coding sequences of the TM and clostridial neurotoxin are preferably arranged in a single genetic construct. These coding sequences are preferably arranged in-frame so that subsequent transcription/translation is continuous through both coding sequences and results in a fusion protein.

Alternatively, the coding sequences of the TM and clostridial neurotoxin may be arranged on separate genetic constructs and, following translation, the corresponding proteins associate with each other to form the agent. Association of the TM and clostridial neurotoxin translation products may be encouraged by ensuring that each translation product has one or more mutually compatible amino acids at an exposed surface. An example of such an amino acid is cysteine, or other sulphur-containing amino acids. The presence of a sulphur group on these amino acids allows the formation of disulphide bridges between the TM end clostridial neurotoxin translation products.

The fusion protein aspect of the present invention may employ any variation of any TM-$LH_N$ sequence identified in the present specifications. For example;

N and C-terminal protein fusions (ie. either 5' or 3' genetic construct fusions) may be employed. Different combinations of TM-$LH_N$, $LH_N$-TM and L-TM-$H_N$ may be more suitable than others;

should a L-TM-$H_N$ fusion be employed then it may be preferable to insert a specific cleavage sequence between the L-chain and TM to enable the TM to have freedom to bind to the target receptor. According to this embodiment it may be preferable to engineer into the genetic construct means (eg. a disulphide bridge) to keep the fusion complex together, the genetic construct preferably incorporates a nucleic acid sequence encoding a spacer peptide at the TM/$LH_N$ fusion junction. However, a spacer is not essential. Examples of spacer peptides include:

PPPIEGR [Kim, J. S., Raines, R. T. (1993). Ribonuclease S-peptide as a carrier in fusion proteins. Protein Sci 2(3):348–56];

collagen-like spacer [Rock, F. Everett, M., Klein, M. (1992). Over-expression and structure-function analysis of a bioengineered IL-2/IL-6 chimeric lymphokine. Protein Eng 5(6):583–91]; and trypsin sensitive diphtheria toxin peptide [O'Hare, M., Brown, A. N., Hussain, K., Gebhardt, A., Watson, G., Roberts, L. M., Vitetta, E. S., Thorpe, P. E., Lord, J. M. (1990). Cytotoxicity of a recombinant ricin-A-chain fusion protein containing a proteolytically-cleavable spacer sequence. FEBS Lett Oct 29;273 (1–2):200–41].

Turning to the clostridial neurotoxin component of the agent, all $LH_N$ variants described in the present application and in the present Applicant's co-pending application U.S. Ser. No. 09/255,829 may be employed. The content of U.S. Ser. No. 09/255,829 is herein Incorporated by reference thereto.

All constructs have a 5' ATG codon to encode an N-terminal methionine and a C-terminal translational stop codon if these codons are not already present. Expression of a number of fusion proteins is well-known in the art and was so at the priority date of the present application Iie. Apr. 21, 1995). Methods for the construction and expression of the constructs of the present invention may employ information from the following references and others:

Lorberboum-Galski, H., FitzGerald, D., Chaudhary, V., Adhya, S., Pastan, I. (1 988). Cytotoxic activity of an interleukin 2-Pseudomonas exotoxin chimeric protein produced in *Escherichia coli*. Proc Natl Acad Sci U S A 85(6):1922–6;

Murphy, J. R. (1988) Diphtheria-related peptide hormone gene fusions: a molecular genetic approach to chimeric toxin development. Cancer Treat Res; 37:123–40;

Williams, D. P., Parker, K., Bacha, P., Bishai, W., Borowski, M., Genbauffe, F., Strom, T. B., Murphy, J. R. (1987). Diphtheria toxin receptor binding domain substitution with interleukin-2: genetic construction and properties of a diphtheria toxin-related interleukin-2 fusion protein. Protein Eng; 1 (6):493–8;

Arora, N., Williamson, L. C., Leppla, S. H., Halpern, J. L. (1994). Cytotoxic effects of a chimeric protein consisting of tetanus toxin light chain and anthrax toxin lethal factor in non-neuronal cells J Biol Chem; 269(42):26165–71;

Brinkmann, U., Reiter, Y., Jung, S. H., Lee, B., Pastan, I. (1993). A recombinant Immunotoxin containing a disulphide-stabilized Fv fragment. Proc Natl Acad Sci U S A;90(16):7538–42, and O'Hare, M., Brown, A. N., Hussain, K., Gebhardt, A., Watson, G., Roberts, L. M., Vitetta, E. S., Thorpe, P. E., Lord, J. M. (1990). Cytotoxicity of a recombinant ricin-A-chain fusion protein containing a proteolytically-cleavable spacer sequence. FEBS Lett Oct 29;273(1–2):200–4.

The method of preparing a fusion protein according to the present invention requires nucleic acid sequence data relating to the selected TM and the clostridial neurotoxin. These sequence data were readily available at the priority date of the present application as evidenced by the data/publications of several preferred TMs which have been listed in the present specification. Alternatively, any necessary sequence data may be obtained by techniques well-known to the skilled person.

In one embodiment, DNA encoding the TM sequences may be cloned from a source organism by screening a cDNA library for the correct coding region (for example by using specific oligonucleotides based on the known sequence information to probe the library), isolating the TM DNA, sequencing this DNA for confirmation purposes, and then placing the isolated DNA in an appropriate expression vector for expression in the chosen host.

As an alternative to isolation of the sequence from a library, the available sequence information may be employed to prepare specific primers for use in PCR, whereby the coding sequence is then amplified directly from the source material and, by suitable use of primers, may be cloned directly into an expression vector.

Another alternative method for isolation of the coding sequence is to use the existing sequence information and synthesise a copy, possibly incorporating alterations, using DNA synthesis technology.

Another alternative method is to use existing protein sequence information and synthesise a version of the coding sequence that can give rise to that protein sequence. Using DNA synthesis technology to do this (and the alternative described above) enables the codon bias of the coding sequence to be modified to be optimal for the chosen expression host. This may give rise to superior expression levels of the fusion protein.

All of the above methods may be employed to obtain sequence information on the selected clostridial neurotoxin component of the agent.

Ideally, optimisation of the codon bias for the expression host would be applied to the TM, the spacer (if there is one), and the $LH_N$ variant. Optimisation of the codon bias is possible by application of the protein sequence into freely available DNA/protein database software, eg. programs available from Genetics Computer Group, Inc.

By way of example, the following TM sequences were readily available by the priority date of the present application (ie. Apr. 21, 1995).

1) Human B-NGF precursor

ULLRICH, A., GRAY, A., BERMAN, C., DULL, T. J. (1983). "Human beta-nerve growth factor gene sequence highly homologous to that of mouse." Nature 303:821–825.

BORSANI, G., PIZZUTI, A., RUGARLI, E. I., FALINI, A., SILANI, V. R. A., SIDOLI, A., SCARLATO, G., BARELLE, F. E. (1990)."CDNA sequence of human beta-NGF." Nucleic Acids Res. 18:4020–4020.

Sequence Data

Mouse beta-nerve growth factor (beta-NGF) MRNA. [ACCESSION K017691] *H. sapiens* gene for beta-nerve growth factor (beta-NGF)- [ACCESSION V01511]

```
Mature NGF sequence =                                          (SEQ ID NO:1)

SSSHPIFHRG EFSVCDSVSV WVGDKTTATD IKGKEVMVLG EVNiNNSVFK
51

OYFFETKCRD PNPVDSGCRG IDSKHWNSVC TTTHTFVKAL TMDGKQAAWR
101

FIRIDTACVC VLSRKAVRRA
```

Back-translated bacterial codon usage sequence for NGF. This, and all of the following sequences, are RNA sequences, and for cloning purposes would need to be the DNA version with T instead of U: (SEQ ID NO: 2)

```
UCCUCCUCCC ACCCGAUCUU CCACCGUGGU GAAUUCUCCG UUUGCGACUC   51

CGUUUCCGUU UGGGUUGGUG ACAAAACCAC CGCUACCGAC AUCAAAGGUA  101

AAGAAGUUAU GGUUCUGGGU GAAGUUAACA UCAACAACUC CGUUUUCAAA  151

CAGUACUUCU UCGAAACCAA AUGCCGUGAC CCGAACCCGG UUGACUCCGG  201

UUGCCGUGGU AUCGACUCCA AACACUGGAA CUCCUACUGC ACCACCACCC  251

ACACCUUCGU UAAAGCUCUG ACCAUGGACG GUAAACAGGC UGCUUGGCGU  301

UUCAUCCGUA UCGACACCGC UUGCGUUUGC GUUCUGUCCC GUAAAGCUGU  351

UCGUCGUGCU
```

The following sequence is the precursor for NGF. This pro-sequence may be useful in certain expression situations. However the mature sequence given above would be preferred.

COMB, M., SEEBURG, P. H., ADELMAN, J., EIDEN, L., HERBERT, E.(1982). "Primary structure of the human Met- and Leu-enkephalin precursor and its MRNA."; Nature 295:663–666.

```
Pro-NGF sequenoe = (SEQ ID NO:3)

MSMLFYTLIT AFLIGIQAEP HSESNVPAGH TIPQVHWTKL QHSLDTALRR   51

ARSAPAAAIA ARVAGQTRNI TVDPRLFKKR RLRSPRVLFS TQPPREAADT  101

QDLDFEVGGA APFNRTHRSK RSSSHPIFHR GEFSVCDSVS VWVGDKTTAT  151

DIKGKEVMVL GEVNINNSVF KQYFFETKCR DPNPVDSGCR GIDSKHWNSY  201

CTTTHTFVKA LTMDGKQAAW RFIRIDTACV CVLSRKAVRR A

Back-translated bacterial codon usage sequence for pro-NGF = (SEQ ID NO:4)

AUGUCCAUGC UGUUCUACAC CCUGAUCACC GCUUUCCUGA UCGGUAUCCA   61

GGCUGAACCG CACUCCGAAU CCAACGUUCC GGCUGGUCAC ACCAUCCCGC  101

AGGUUCACUG GACCAAACUG CAGCACUCCC UGGACACCGC UCUGCGUCGU  151

GCUCGUUCCG CUCCGGCUGC UGCUAUCGCU GCUCGUGUUG CUGGUCAGAC  201

CCGUAACAUC ACCGUUGACC CGCGUCUGUU CAAAAAACGU CGUCUGCGUU  251

CCCCGCGUGU UCUGUUCUCC ACCCAGCCGC CGCGUGAAGC UGCUGACACC  301

CAGGACCUGG ACUUCGAAGU UGGUGGUGCU GCUCCGUUCA ACCGUACCCA  351

CCGUUCCAAA CGUUCCUCCU CCCACCCGAU CUUCCACCGU GGUGAAUUCU  401

CCGUUUGCGA CUCCGUUUCC GUUUGGGUUG GUGACAAAAC CACCGCUACC  451

GACAUCAAAG GUAAAGAAGU UAUGGUUCUG GGUGAAGUUA ACAUCAACAA  501

CUCCGUUUUC AAACAGUACU UCUUCGAAAC CAAAUGCCGU GACCCGAACC  551

CGGUUGACUC CGGUUGCCGU GGUAUCGACU CCAAACACUG GAACUCCUAC  601

UGCACCACCA CCCACACCUU CGUUAAAGCU CUGACCAUGG ACGGUAAACA  651

GGCUGCUUGG CGUUUCAUCC GUAUCGACAC CGCUUGCGUU UGCGUUCUGU  701

CCCGUAAAGC UGUUCGUCGU GCU
```

2) Enkephalin

NODA, M., TERANISHI Y., TAKAHASHI, H., TOYOSATO, M., NOTAKE, M., NAKANISHI, S., NUMA, S. (1982). "Isolation and structural organisation of the human preproenkephalin gene."; Nature 297:431–434.

Sequence Data

Leu-enkephalin=YGGFL (SEQ ID NO: 5) therefore a corresponding bacterial coding sequence would be
1 (SEQ ID NO: 6) UACGGUGGUU UCCUG Met-enkephalin=YGGFM (SEQ ID NO: 7) therefore a corresponding bacterial coding sequence would be
1 (SEQ ID N): 8) UACGGUGGUU UCAUG 3) Bradykinin TAKAGAKI, Y., KITAMURA, N., NAKANISHI, S. (1985). "Cloning and sequence analysis of cDNAS for human high molecular weight and low molecular weight prekininogens. Primary structures of two human Prekininogens."; J. Biol. Chem. 260:8601–8609.

Sequence Data

Protein sequence=RPPGFSPFR (SEQ ID NO: 9) therefore a corresponding bacterial coding sequence would be (SEQ ID NO: 10)

CGUCCGCCGG GUUUCUCCCC GUUCCGU

In another embodiment of the invention the required $LH_N$, which may be a hybrid of an L and $H_N$ from different clostridial toxin types, is expressed recombinantly as a fusion protein with the TM, and may also include one or more spacer regions.

In another embodiment of the invention the light chain of a clostridial neurotoxin, or a fragment of the light chain containing the endopeptidase activity, is expressed recombinantly as a fusion protein with a TM which can also affect the internalization of the light chain, or fragment thereof containing the endopeptidase activity, into the cytoplasm of the cell. The expressed fusion protein may also include one or more spacer regions.

The basis of this disclosure is the creation of novel agents with very specific and defined activities against a limited and defined class of neurons (primary sensory afferents), and as such the agents may be considered to represent a form of neurotoxin. The therapeutic use of native botulinum neurotoxins is well known in the prior art. The mode of action of the botulinum neurotoxins, as described in the prior art, however, is by a mechanism, inhibition of acetylcholine secretion, and against a category of target neurons, efferent motorneurons, clearly distinct from the agents described in this disclosure. The prior art does not teach either the activity or the chemical structure of the agents disclosed. Thus, although, as discussed in this application, the prior art teaches much about the native clostridial neurotoxins, native unmodified clostridial neurotoxins are not the subject of this disclosure. The agent of this invention requires modification of the clostridial neurotoxins such that the targeting property taught in the prior art is removed. The modified neurotoxin is then coupled to a new targeting function (the TM), to give a novel agent with new biological properties distinct from those of the native clostridial neurotoxins and not taught in the prior art. It is this new agent with novel properties that is the subject of this disclosure.

EXPLOITATION IN INDUSTRY

The agent described in this invention can be used in vivo, either directly or as a pharmaceutically acceptable salt for treatment of pain.

For example, an agent according to the invention can be used systemically for the treatment of severe chronic pain. A specific example of this is the use in treatment of clinical pain associated with rheumatoid arthritis affecting multiple joints.

In another example, an agent according to the invention can be locally applied for the treatment of pain. A specific example of this is treatment by local injection into a joint affected by inflammatory pain.

In further example an agent according to the invention can be administered by spinal injection (epidural or intrathecal) at the level of the spinal segment involved in the innervation of an affected organ for the treatment of pain. This is, for example, applicable in the treatment of deep tissue pain, such as chronic is malignant pain.

The present invention will now be illustrated by reference to the following non-limiting examples:

EXAMPLE 1

Synthesis of a Conjugate of NGF and the $LH_N$ Fragment of BoNT/A

Lyophilised murine 2.5 S NGF was dissolved by the addition of water and dialysed into MES buffer (0.1 M MES, 0.1 M sodium chloride, pH 5.0). To this solution (at a concentration of about 0.3 mg/ml) was added PDPH (100 mg/ml in DMF) to a final concentration of 1 mg/ml. After mixing, solid EDAC was added to produce a final concentration of about 0.2 mg/ml. The reaction was allowed to proceed for at least 30 min at room temperature. Excess PDPH was then removed by desalting over a PD-10 column (Pharmacia) previously equilibrated with MES buffer.

The $LH_N$ fragment of BoNT/A was produced essentially by the method of Shone C. C., Hambleton, P., and Melling, J. 1987, Eur. J. Biochem. 167, 175–180. An amount of $LH_N$ equivalent to half the weight of NGF used dissolved in triethanolamine buffer (0.02 M triethanolamine/HCl, 0.1 M sodium chloride, pH 7.8) at a concentration of about 1 mg/ml, was reacted with Traut's reagent (100 mM stock solution in 1 M triethanolamine/HCl, pH 8.0) at a final concentration of 2 mM. After one hour the $LH_N$ was desalted into PBSE (phosphate buffered saline with 1 mM EDTA) using a PD-10 column (Pharmacia). The protein peak from the column eluate was concentrated using a Microcon 50 (Amicon) to a concentration of about 2 mg/ml.

The derivatized NGF was subjected to a final concentration step resulting in a reduction in volume to less than 10% of the starting volume and then mixed with the derivatized $LH_N$ overnight at room temperature. The products of the reaction were analysed by polyacrylamide gel electrophoresis in the presence of sodium dodecyl-sulphate (SDS-PAGE).

The conjugate resulting from the above reaction was partially purified by size exclusion chromatography over Bio-Gel P-100 (Bio-Rad). The elution profile was followed by measuring the optical density at 280 nm and SDS-PAGE analysis of the fractions. This allowed the separation of conjugate from free NGF and by-products of the reaction.

FIG. 1 shows the SDS-PAGE analysis of the fractions from one such Bio-Gel P-100 column. The free $LH_N$ and conjugate ($M_r$ 100 kDa and above) are clearly separated from the majority of the free NGF ($M_r$ 13 kDa). As 2.5 S NGF is a homo-dimer formed by non-covalent interactions it is dissociated by treatment with SDS. Thus molecules that have formed covalent cross-links to $LH_N$ through one subunit only will dissociate during the SDS-PAGE analysis and give rise to the free NGF band seen in fractions 4–6. This result demonstrates that the homo-dimeric structure of NGF remains intact after derivatisation. The free $LH_N$ seen in these fractions represents a minor component which has not coupled to NGF. Fractions 4–6 were pooled before further analysis.

Figure 2:
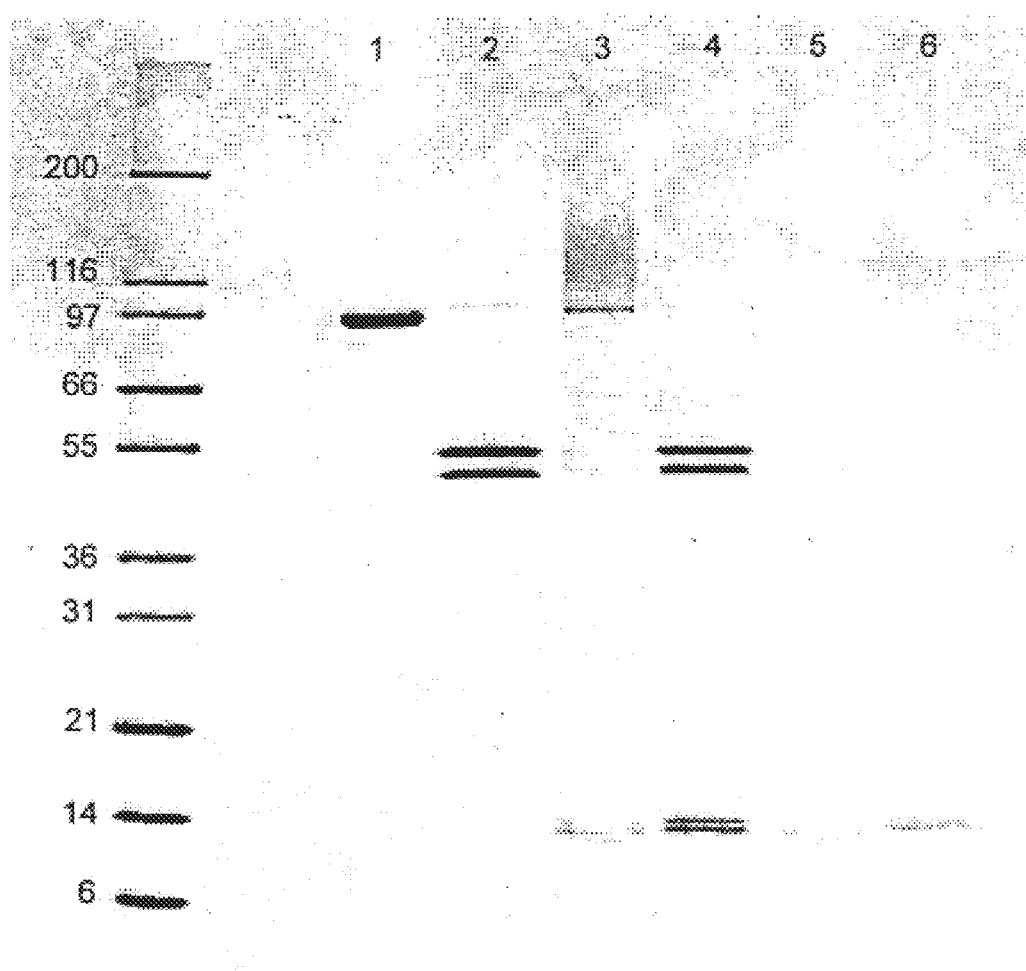
FIG. 2 shows a Coomassie stain of an SDS-PAGE analysis of the conjugate of NGF and $LH_N$ under reducing and non-reducing conditions.

FIG. 2 shows an analysis of the conjugate by SDS-PAGE under reducing and non-reducing conditions. Lane 1 is free $LH_N$ under non-reducing conditions, lane 2 is the same amount of $LH_N$ reduced with 50 mM dithiothreitol. Lanes 3 and 4 show the conjugate after size exclusion chromatography either without (lane 3) or with (lane 4) reduction by dithiothreitol. Similarly, lanes 5 and 6 show NGF without or with reduction respectively. The results clearly show that the material in lane 5 with an apparent molecular mass greater than 100 kDa produces, upon reduction, the constituent bands of $LH_N$ and NGF only. Furthermore the intensity of the bands following reduction is such that they must be derived from material other than the small amounts of free $LH_N$ and NGF observed in the unreduced sample. The only available source for the excess is the material with an apparent molecular mass>100 kDa. The conjugate in the fractions obtained following the size-exclusion chromatography thus represents NGF and $LH_N$ covalently linked by reducible disulphide linkages.

The fractions containing conjugate were stored at 4° C. until required.

EXAMPLE 2

Activities of a Conjugate of NGF and $LH_N$ in PC-12 Cells

PC12 cells are a cell-line of neuroectodermal derivation that are commonly used as a model system for the study of nerve function. As a model system for testing the function of a conjugate of NGF and $LH_N$ they have two necessary features: firstly they are well known to possess cell-surface receptors for NGF that have been shown to be involved in a differentiation process in response to low concentrations of NGF. Secondly they have been shown to contain the exocytotic machinery for neurotransmitter release including, importantly in this example, SNAP-25.

PC12 cells were plated out into a 24-well plate that had been coated with MATRIGEL basement membrane matrix (Collaborative Biomedical Products) at a density of approximately $5 \times 10^5$ cells per well. After a few days in culture (RPMI 1640 with 2 mM glutamine, 10% horse serum and 5% foetal calf serum, 37° C., 5% $CO_2$) the medium was replaced with fresh medium containing added conjugate (prepared as described in Example 1) or $LH_N$ or no addition. After being kept in culture overnight the medium was removed and the cells washed once with fresh medium. Cells were then lysed by the addition of 0.45 ml sodium hydroxide (0.2 M) for 30 min. After this time the solutions were neutralised by the addition of 0.45 ml hydrochloric acid (0.2 M) followed by 0.1 ml of HEPES/NaOH (1 M, pH 7.4). To extract the membrane proteins from these mixtures Triton-X-114 (10%, v/v) was added and incubated at 4° C. for 60 min, the insoluble material was removed by centrifugation and the supernatants were then warmed to 37° C. for 30 min. The resulting two phases were separated by centrifugation and the upper phase discarded. The proteins in the lower phase were precipitated with chloroform/methanol for analysis by Western blotting.

Figure 3:
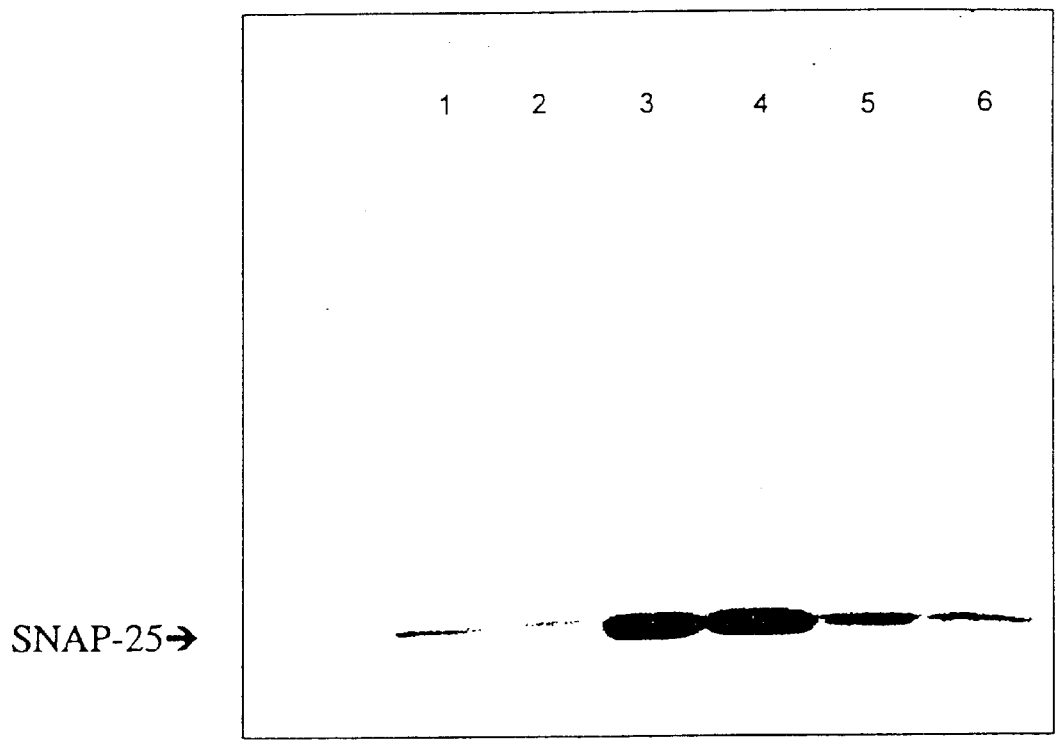
FIG. 3 shows a Western blot of extracts from PC12 cells treated with the conjugate of NGF and $LH_N$, probed with an antibody that recognises the product of the proteolysis of SNAP-25 by the L-chain of BoNT/A.
Figure 4:
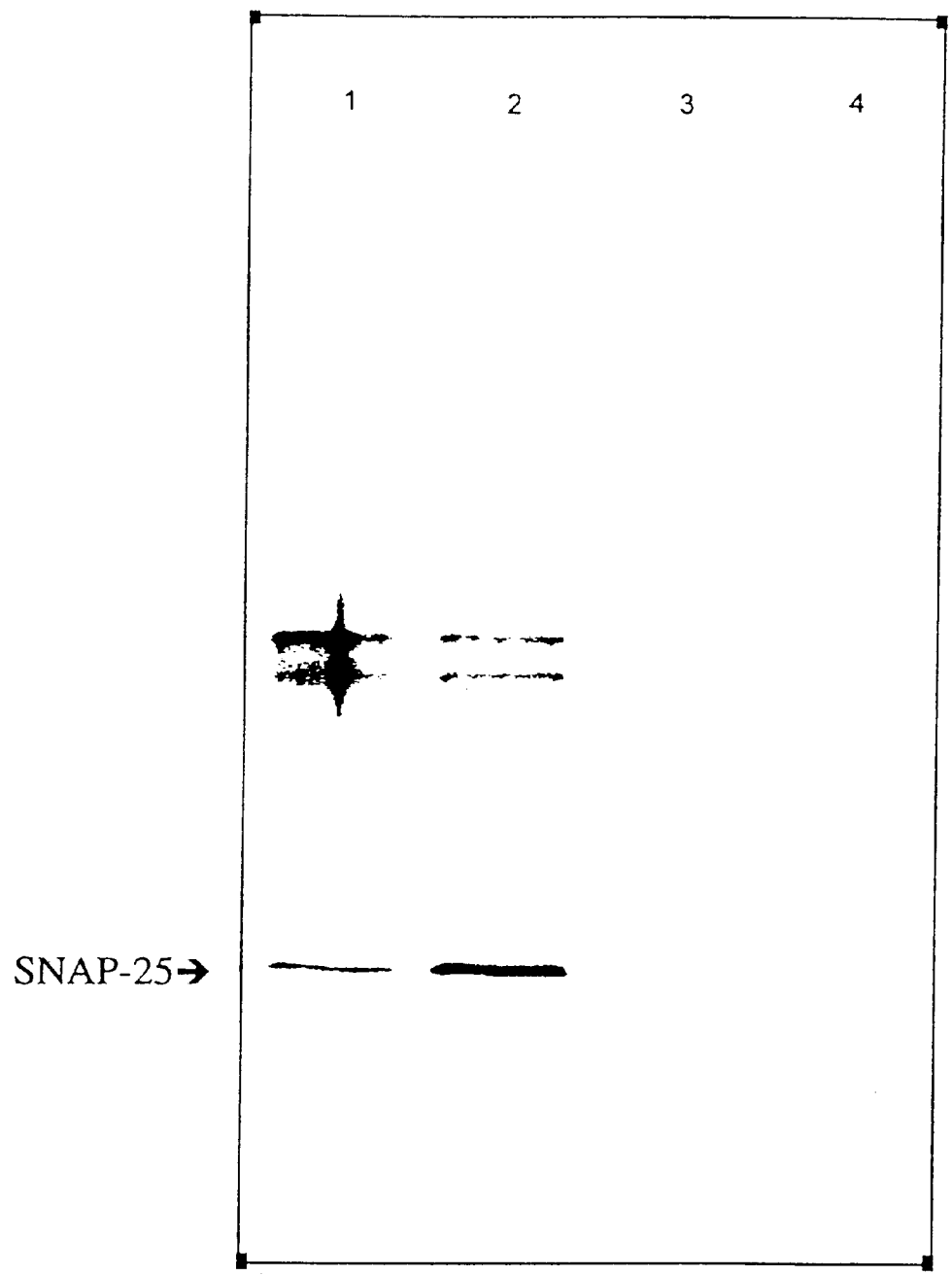
FIG. 4 shows a Western blot of extracts from rat dorsal root ganglion neurons treated with the conjugate of NGF and $LH_N$, probed with an antibody that recognises the product of the proteolysis of SNAP-25 by the L-chain of BoNT/A.

The samples were separated by SDS-PAGE and transferred to nitro-cellulose. Proteolysis of SNAP-25, a crucial component of the neurosecretory process and the substrate for the zinc-dependent endopeptidase activity of BoNT/A, was then detected by probing with an antibody that recognises the newly revealed carboxy-terminus of the cleaved SNAP-25 (the antibody is described in Patent Application PCT/GB95/01279). FIG. 3 shows an example of such a Western blot. No significant immunoreactivity was observed in samples from control cells (lanes 1 and 2) whereas a band corresponding to a molecular mass of 29 kDa was observed weakly in samples incubated with 10 mg/ml $LH_N$ (lanes 5 and 6) and strongly in samples incubated with 10 mg/ml of the conjugate of NGF and $LH_N$ (lanes 3 and 4). Thus incubation of PC12 cells with the conjugate leads to the marked proteolysis of SNAP-25 indicting that the conjugate has introduced the zinc-dependent proteolytic activity of the L-chain of BoNT/A into the cells' cytoplasm. Little or no such activity was seen with the constituent components of the conjugate.

Incubation of cells with the conjugate in the presence of an excess of free NGF resulted in a reduced production of the proteolytic product of SNAP-25 than did incubation with the conjugate alone. This indicates that the action of the conjugate occurs by means of the NGF targeting moiety interacting with the cell surface receptors for NGF.

EXAMPLE 3

The Activity of a Conjugate of NGF and $LH_N$ in Primary Cultures of Dorsal Root Ganglion Neurons The dorsal root ganglia contain the cell bodies of primary nociceptive afferents. It is well established that in primary in vitro cultures of this tissue the neurons retain many of the characteristics of the nociceptive afferents. These characteristics include the ability to release neuropeptides such as substance P in response to chemical stimuli known to cause pain in vivo (e.g. capsaicin). Furthermore the neurons are known to possess receptors for NGF.

Primary cultures of dorsal root ganglion neurons were established following dissociation of the ganglia dissected from rat embryos (embryological age 12–15 days). The cells were plated into 12 well plates at an initial density of $3 \times 10^5$ cells/well in a medium containing NGF (100 ng/ml). After one day in culture fresh medium containing cytosine arabinoside (10 mM) was added to kill non-neuronal cells. The cytosine arabinoside was removed after 2–4 days. After several more days in culture the medium was replaced with fresh medium containing conjugate or $LH_N$ in the absence of NGF. Following overnight incubation at 37° C. the medium was removed, the cells were lysed and the hydrophobic proteins extracted using Triton-X-114 as described in Example 2.

The samples were analysed by Western blotting as described in Example 2 with the antibody that recognises the product of the BoNT/A proteolysis of SNAP-25. No immunoreactivity was observed in samples from control cells (lane 4) whereas a band corresponding to a molecular mass of 29 kDa was observed weakly in samples incubated with 10 mg/ml $LH_N$ (lane 3) and strongly in samples incubated with 10 mg/ml of the conjugate of NGF and $LH_N$ (lanes 1 and 2).

This result indicates that the conjugate can deliver the proteolytically-active L-chain of BoNT/A into the cytoplasm of the neuronal cells that, in vivo, form the primary nociceptive afferents.

EXAMPLE 4

The Production of a Chimeric $LH_N$ Whereof the L chain is Derived from BoNT/B and the $H_N$ Fragment from BoNT/A The $H_N$ fragment of BoNT/A is produced according to the method described by Shone C. C., Hambleton, P., and Melling, J. (1987, *Eur. J. Biochem*. 167, 175–180) and the L-chain of BoNT/B according to the method of Sathyamoorthy, V. and DasGupta, B. R. (1985, *J. Biol. Chem*. 260, 10461–10466). The free cysteine on the $H_N$ fragment of BoNT/A is then derivatised by the addition of a ten-fold molar excess of dipyridyl disulphide followed by incubation at 4° C. overnight. The excess dipyridyl disulphide and the thiopyridone by product are then removed by desalting the protein over a PD10 column (Pharmacia) into PBS.

The derivatised $H_N$ is then concentrated to a protein concentration in excess of 1 mg/ml before being mixed with an equimolar portion of L-chain from BoNT/B (>1 mg/ml in PBS). After overnight incubation at room temperature the mixture is separated by size exclusion chromatography over Superose 6 (Pharmacia), and the fractions analysed by SDS-PAGE. The chimeric $LH_N$ is then available for derivatisation to produce a targeted conjugate as described in Example 1.

EXAMPLE 5

A Method for Expression of a Protein Fusion Construct

The following references relate to the expression of recombinant NGF:

Dicou, E. (1 992) Expression of recombinant human nerve growth factor in *Escherichia coli*, Neurochem Int. 20, 129–134; and Fujimori, K et al. (1992) Overproduction of biologically-active human nerve growth factor in *Escherichia coli*, Biosci-Biotechnol-Biochem, 56, 1985–1990.

This example describes how to make a NGF-$LH_N$/A fusion construct.

The coding region for mature NGF is placed in frame with the coding sequence for $LH_N$/A such that translation of protein is continuous through the NGF and into $LH_N$/A coding sequence.

Translation is initiated by incorporation of the codon for an N-terminal methionine (ATG) immediately before the NGF sequence.

Translation is terminated by Incorporation of a STOP codon (TGA, TAA or TAG) immediately after the $LH_N$/A coding sequence, unless it is preferred to use a C-terminal tag to facilitate purification of the fusion protein, in which case no STOP codon would be inserted and translation would continue into the tag.

The entire DNA expression cassette is then cloned into, for example, a vector suitable for expression of proteins in *E. coli*. Expression of the protein is achieved by induction of transcription and the synthesised protein is isolated from the host cell by classical purification techniques.

Incorporation of an affinity tag would facilitate this last step.

The examples described above are purely illustrative of the invention. In synthesizing the agent the coupling of the TM to the modified clostridial neurotoxin or fragment thereof is achieved via chemical coupling using reagents and techniques known to those skilled in the art. Thus, although the examples given use exclusively the PDPH/EDAC and Traut's reagent chemistry any other coupling chemistry capable of covalently attaching the TM component of the agent to clostridial neurotoxin derived component and known to those skilled in the art is covered by the scope of this application. Similarly it is evident to those skilled in the art that either the DNA coding for either the entire agent or fragments of the agent could be readily constructed and, when expressed in an appropriate organism, could be used to recombinantly produce the agent or fragments of the agent. Such genetic constructs of the agent of the invention obtained by techniques known to those skilled in the art are also covered in the scope of this invention.

TABLE I

Possible Targeting Moieties (TM)

Growth Factors:

1. Nerve growth factor (NGF);
2. Leukaemia inhibitory factor (LIF);
3. Basic fibroblast growth factor (bFGF);
4. Brain-derived neurotrophic factor (BDNF);
5. Neurotrophin-3 (NT-3);
6. Hydra head activator peptide (HHAP);
7. Transforming growth factor 1 (TGF- 1);
8. Transforming growth factor 2 (TGF- 2);
9. Transforming growth factor (TGF-);
10. Epidermal growth factor (EGF);
11. Ciliary neuro-trophic factor (CNTF).

Cytokines:

1. Tumour necrosis factor (TNF-);
2. Interleukin-1 (IL-1);
3. Interleukin-1 (IL-1);
4. Interleukin-8 (IL-8).

Peptides:

1. -Endorphin;
2. Methionine-enkephalin;
3. D-Ala$^2$-D-Leu$^5$-enkephalin;
4. Bradykinin.

Antibodies:

1. Antibodies against the lactoseries carbohydrate epitopes found on the surface of dorsal root ganglion neurons (e.g. monoclonal antibodies 1B2 and LA4);
2. Antibodies against any of the receptors for the ligands given above.
3. Antibodies against the surface expressed antigen Thy1 (e.g. monoclonal antibody MRC OX7).

What is claimed is:

1. A method for preparing an agent in the form of a fusion protein, which agent binds to a peripheral sensory afferent, the agent comprising a Targeting Moiety (TM) coupled to a modified clostridial neurotoxin in which the TM comprises a ligand to a cell-surface binding site present on a primary sensory afferent and is capable of functionally interacting with the binding site causing a physical association between the agent and the surface of the primary sensory afferent, wherein the heavy chain (H-chain) of the clostridial neurotoxin is removed or modified to remove or reduce its native binding affinity for motor neurons, and the light chain (L-chain) of the clostridial neurotoxin or a fragment thereof retains a protease activity specific for components of the neurosecretory machinery, the TM and the modified H-chain, if present, forming a molecule which introduces the L-chain or fragment thereof into the cytosol of a primary sensory afferent, thereby inhibiting the transmission of signals between a primary sensory afferent and a projection neuron by controlling the release of at least one neurotransmitter or neuromodulator from the primary sensory afferent;

said method comprising expressing in a host organism a genetic construct which codes for the agent.

2. A method according to claim 1 which further comprises constructing the genetic construct and transforming the host with said construct.

3. A method according to claim 1, wherein the genetic construct includes a sequence encoding a spacer molecule by which the modified clostridial neurotoxin, or a fragment thereof, is coupled to the TM.

4. A method according to claim 3, wherein the spacer molecule is selected from the group consisting of (SEQ ID NO: 11) PPPIEGR, collagen-like spacer, and trypsin-sensitive diphtheria toxin peptide.

5. A method according to claim 1, wherein the nucleic acid sequence of the genetic construct is modified in accordance with the codon bias of the host cell.

6. A method according to claim 1, wherein the genetic construct incorporates a nucleic acid sequence encoding an affinity tag to facilitate purification of the assembled toxin.

7. An agent which binds to a peripheral sensory afferent and has been obtained in the form of a fusion protein by the method according to claim 1, said agent comprising a Targeting Moiety (TM) coupled to a modified clostridial neurotoxin in which the TM comprises a ligand to a cell-surface binding site present on a primary sensory afferent and is capable of functionally interacting with the binding site causing a physical association between the agent and the surface of the primary sensory afferent, wherein the heavy chain (H-chain) of the clostridial neurotoxin is removed or modified to remove or reduce its native binding affinity for motor neurons, and the light chain (L-chain) of the clostridial neurotoxin or a fragment thereof retains a protease activity specific for components of the neurosecretory machinery, the TM and the modified H-chain, if present, forming a molecule which introduces the L-chain or fragment thereof into the cytosol of a primary sensory afferent, thereby inhibiting the transmission of signals between a primary sensory afferent and a projection neuron by controlling the release of at least one neurotransmitter or neuromodulator from the primary sensory afferent.

\* \* \* \* \*